(12) United States Patent
Haraga et al.

(10) Patent No.: US 9,110,047 B2
(45) Date of Patent: Aug. 18, 2015

(54) COMPOUND FOR FORMING FLUORESCENT URANIUM COMPLEX, METHOD FOR SYNTHESIZING THEREOF, FLUORESCENT PROBE FOR DETECTING URANIUM AND METHOD FOR ANALYZING URANIUM

(71) Applicant: JAPAN ATOMIC ENERGY AGENCY, Ibaraki (JP)

(72) Inventors: Tomoko Haraga, Naka-gun (JP); Shingo Saito, Saitama (JP); Yoshiyuki Sato, Saitama (JP)

(73) Assignee: JAPAN ATOMIC ENERGY AGENCY, Ibaraki (JP)

( * ) Notice: Subject to any disclaimer, the term of this patent is extended or adjusted under 35 U.S.C. 154(b) by 436 days.

(21) Appl. No.: 13/748,953

(22) Filed: Jan. 24, 2013

(65) Prior Publication Data

US 2013/0217135 A1     Aug. 22, 2013

(30) Foreign Application Priority Data

Feb. 21, 2012    (JP) ................................. 2012-034711

(51) Int. Cl.
    *G01N 33/20*       (2006.01)
    *C07D 471/04*     (2006.01)
             (Continued)

(52) U.S. Cl.
CPC .............. *G01N 33/20* (2013.01); *C07D 471/04* (2013.01); *G01N 21/6428* (2013.01); *G01N 27/44726* (2013.01)

(58) Field of Classification Search
CPC ...... G01N 33/20; G01N 31/22; G01N 33/582
USPC ..................................................... 436/82, 81
See application file for complete search history.

(56) References Cited

U.S. PATENT DOCUMENTS 5,827,653 A * 10/1998 Sammes et al. .............. 435/6.11

FOREIGN PATENT DOCUMENTS

JP    2009-150650 A    7/2009
JP    2009-168450 A    7/2009

OTHER PUBLICATIONS

Novel Monoclonal Antibodies with Specificity for Chelated Uranium(VI): Isolation and Binding Properties Robert C. Blake II, Andrey R. Pavlov, Mehraban Khosraviani, Harry E. Ensley, Garry E. Kiefer, Haini Yu, Xia Li, Diane A. Blake Bioconjugate Chem. 2004, 15, 1125-1136.*

(Continued)

*Primary Examiner* — Krishnan S Menon
*Assistant Examiner* — Dwan A Gerido
(74) *Attorney, Agent, or Firm* — Westerman, Hattori, Daniels & Adrian, LLP

(57) ABSTRACT

Disclosed is a compound suitable for use as a fluorescent probe for the detection of uranium. The compound enables the qualitative and quantitative analysis of uranium present in waste samples using less expensive apparatuses. The compound of the present invention has the structure shown by the following formula.

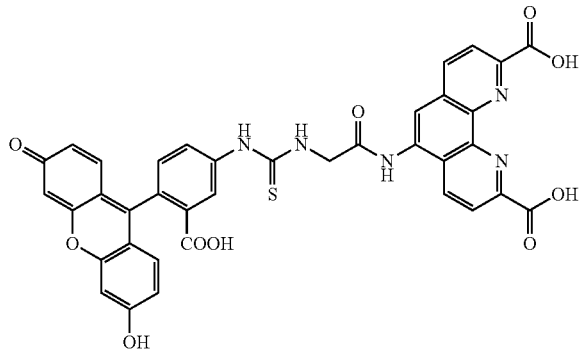

4 Claims, 3 Drawing Sheets

(51) Int. Cl.
*G01N 27/447* (2006.01)
*G01N 21/64* (2006.01)
*G01N 33/22* (2006.01)

(56) References Cited

OTHER PUBLICATIONS

Enhancement of Luminescence of Europium(III) Ions in Water by use of Synergistic Chelation. Part 1. 1:1 and 2:1 Complexes John Coates, Peter G. Sammes, and Richard M. West J. Chem. Soc., Perkin Trans. 2, 1996.*

Enhancement of Luminescence of Europium(III) Ions in Water by use of Synergistic Chelation. Part 2. 1:1 and 2:1 Complexes John Coates, Peter G. Sammes, and Richard M. West J. Chem. Soc., Perkin Trans. 2, 1996.*

Preparation of Some New Intercalating Europium(III) Sensitizers Stephen T. Mullins, Peter G. Sammes, Richard M. West, and Gokhan Yahioglu J. Chem. Soc., Perkin Trans. 1.*

Blake et al., "Antibody-based sensors for heavy metal ions", Biosensors & Bioelectronics, vol. 16, 2001, pp. 799-809.

* cited by examiner

COMPOUND FOR FORMING FLUORESCENT URANIUM COMPLEX, METHOD FOR SYNTHESIZING THEREOF, FLUORESCENT PROBE FOR DETECTING URANIUM AND METHOD FOR ANALYZING URANIUM

BACKGROUND OF THE INVENTION

1. Field of the Invention

The present invention relates to compounds capable of forming stable fluorescent uranium complexes, methods for synthesizing thereof, fluorescent probes for detecting uranium formed of such compounds, and methods for analyzing uranium using such probes.

2. Description of the Related Art

Uranium compounds may be present in liquid and solid wastes generated from nuclear facilities such as nuclear power plants and research facilities using radioactive materials. If uranium is present in the liquid and solid wastes, its concentration must be determined before these wastes are disposed of. Traditionally, uranium present in the wastes has been determined by mass spectrometry after isolated from the wastes by using complicated isolation procedures such as ion-exchange and solvent extraction. The detection limit of uranium by mass-spectrometry has been in the order of parts-per-trillion (ppt) to parts-per-quadrillion (ppq) (i.e., $10^{-12}$ to $10^{-10}$M). However, equipment used for mass-spectrometry is quite expensive and susceptible to contamination by a variety of radionuclides present in the wastes.

On the other hand, a method for qualitatively and quantitatively analyzing a metal ion present in a sample solution has been developed in which a metal detection fluorescent probe having a "ligand-spacer-fluorophore" structure is mixed with a metal-containing sample to form a fluorescent metal complex, which is subsequently separated by gel electrophoresis for qualitatively and quantitatively analyzing the metal present in the sample (See, for example, Patent Articles 1 (JP 2009-150650 A) and 2 (JP 2009-168450 A)). Specifically, the following ligands are used in this approach: 2-(4-fluorescein-thiocarbamyl-aminobenzyl)-ethylenediamine tetraacetic acid (FTC-ABEDTA), 2-(4-fluorescein-thiocarbamyl-aminobenzyl)-1,4,7,10-tetraazacyclododecane-1,4,7,10-tetraacetic acid (FTC-AB-DOTA), 2-(4-fluorescein-thiocarbamyl-aminobenzyl)-diethylenetriamine pentaacetic acid (F1C-ABDTPA), and N-[(R)-2-amino-3-(p-fluorescein-thiocarbamyl-phenyl) propyl]-trans-(S,S)-cyclohexan e-1,2-diamine-N,N',N',N",N"-pentaacetic acid (FTC-CHX-A"-DTPA). The inventors of the present invention have used each of these ligands to form a fluorescent uranium complex with $UO_2^{2+}$ ion present in a sample, which was then subjected to electrophoresis for qualitatively and quantitatively analyzing uranium present in the sample. However, these fluorescent uranium complexes are highly unstable that they quickly decompose into the probe and the metal, making it a challenge to qualitatively and quantitatively analyze uranium present in samples.

Meanwhile, an attempt has been made to provide compounds that are capable of forming stable complexes with $UO_2^{2+}$ ion (See, Non-Patent Article 1 (Diane A. Blake et al, Biosensors & Bioelectronics 16, 2001, p 799-809)).

BRIEF SUMMARY OF THE INVENTION

Although significant effort has been made to provide a method for qualitatively and quantitatively analyzing uranium present in uranium-containing wastes using less expensive apparatuses, no such methods have existed to date.

Thus, it is an object of the present invention to provide a compound capable of forming a stable fluorescent uranium complex, as well as a method for synthesizing such a compound.

It is another objective of the present invention to provide a fluorescent probe for detecting uranium composed of the above-described compound, as well as a less expensive method for qualitatively and quantitatively analyzing uranium using such a probe.

In an effort to achieve the above-described objects, the present inventors have found that specific compounds are capable of forming stable complexes with uranium. It is this finding that has ultimately led to the present invention.

A compound of the present invention is 5-(2-(3-(3-carboxy-4-(3-hydroxy-6-oxo-6H-xanthen-9-yl)phenyl)thioureido)acetamido) 1,10-phenanthroline-2,9-dicarboxylic acid (FTC-PDA) as shown by the following formula:

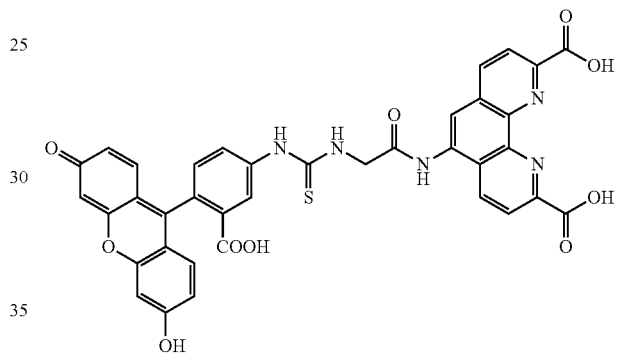

One method for synthesizing the compound of the present invention includes the following Steps (a) through (d):

Step (a) in which the compound of the following formula (1) is reacted with hydrogen to obtain the compound of the following formula (2);

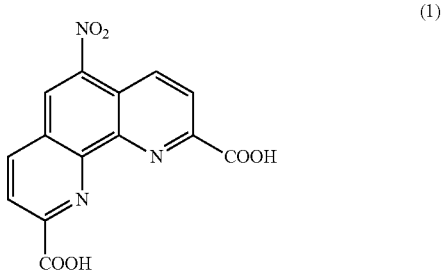

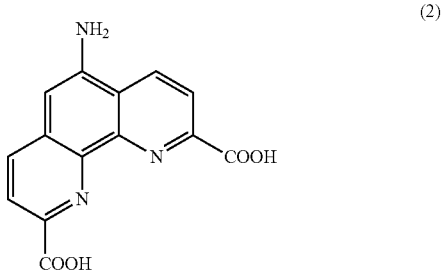

Step (b) in which the compound of the formula (2) is reacted with chloroacetyl chloride to obtain the compound of the following formula (3);

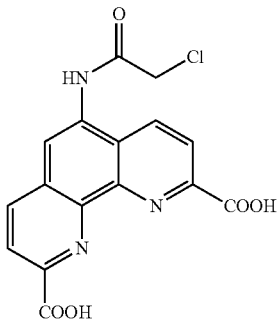

(3)

Step (c) in which the compound of the formula (3) is reacted with aqueous ammonia to obtain the compound of the following formula (4); and

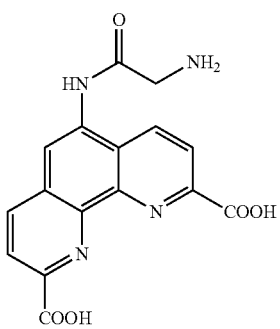

(4)

Step (d) in which the compound of the formula (4) is reacted with fluorescein-4-isocyanate of the following formula (5).

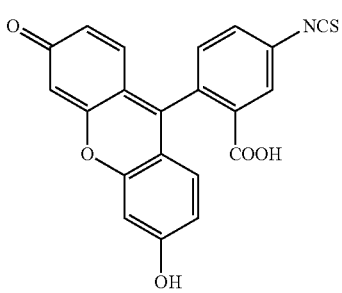

(5)

A uranium detection fluorescent probe of the present invention is formed of the above-described compound.

One method for qualitatively and quantitatively analyzing uranium according to the present invention includes the following Steps (A) through (C):

Step (A) in which a sample containing uranium is mixed with the above-described fluorescent probe for detecting uranium to form a fluorescent uranium complex in the resulting mixture;

Step (B) in which the mixture containing the fluorescent uranium complex is subjected to capillary electrophoresis; and Step (C) in which the intensity of the fluorescence is measured.

The compound of the present invention is capable of forming a stable fluorescent uranium complex with $UO_2^{2+}$ ion. The method for qualitatively and quantitatively analyzing uranium according to the present invention can be carried out by using only trace amounts of samples and less expensive apparatuses and results in little or no contamination of the apparatuses by uranium. The detection limit for uranium by the method of the present invention is in the order of several tens of parts per trillion (ppt).

BRIEF DESCRIPTION OF THE SEVERAL
VIEWS OF THE DRAWINGS

DETAILED DESCRIPTION OF THE INVENTION

A method for synthesizing the compound of the present invention will now be described with reference to FIG. 1.

First, the compound of the above-described formula (1) is synthesized according to the method described in Bioconjugate Chem., Vol. 15, No. 5, 2004, p 1125-1136.

Figure 1:
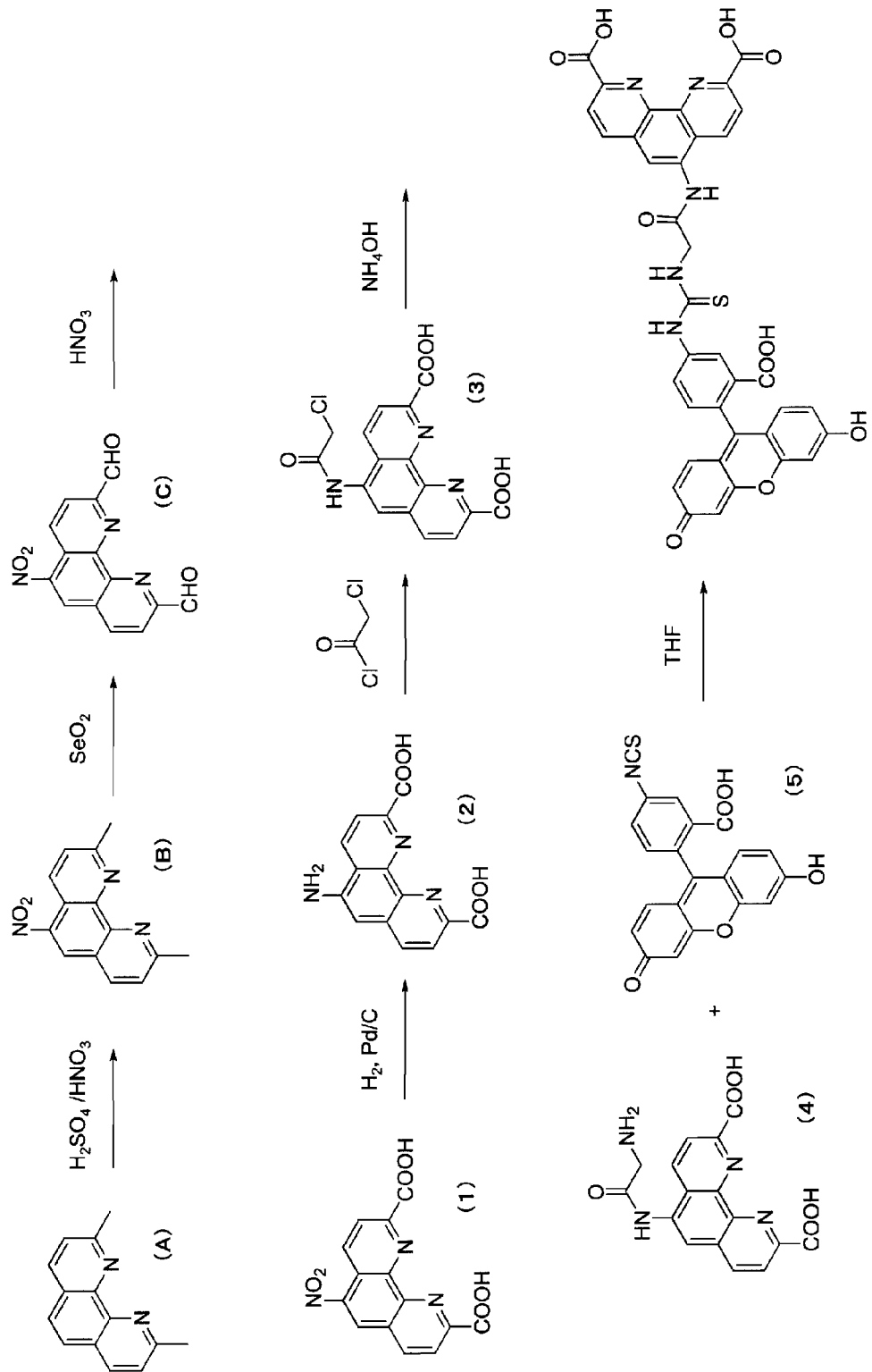
FIG. 1 illustrates a part of one method of synthesizing a compound of the present invention.

Specifically, 2,9-dimethyl-1,10-phenanthroline shown by the formula (A) in FIG. 1 is reacted with an acid mixture composed of nitric acid and sulfuric acid to give 5-nitro-2,9-dimethyl-1,10-phenanthroline shown by the formula (B) in FIG. 1. The 5-nitro-2,9-dimethyl-1,10-phenanthroline is then reacted with selenium dioxide to give a dialdehyde compound shown by the formula (C) in FIG. 1. This dialdehyde compound is then oxidized to obtain the compound of the formula (1).

The resulting compound of the formula (1) is then reduced by hydrogen to give the compound of the formula (2). The compound of the formula (2) is then reacted with chloroacetyl chloride to give the compound of the formula (3). The compound of the formula (3) is then reacted with aqueous ammonium to give the compound of the formula (4). The compound of the formula (4) is then reacted with fluorescein-4-isocyanate of the formula (5) to obtain FTC-FDA.

Figure 2:
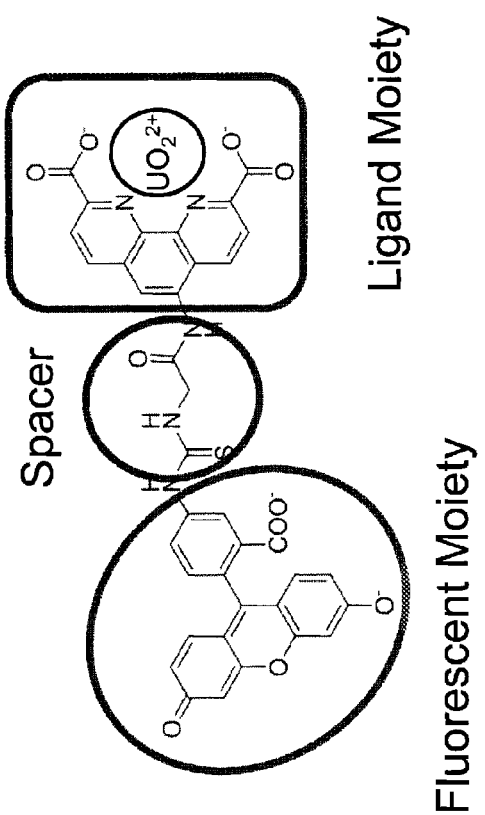
FIG. 2 illustrates a fluorescent uranium complex formed of the compound of the present invention and $UO_2^{2+}$ ion.

FTC-PDA forms a stable uranium complex with $UO_2^{2+}$ ion. When irradiated with laser light, the complex emits fluorescence. This makes FTC-PDA suitable for use as a fluorescent probe for the detection of uranium. It is believed that the complex has the (fluorescent moiety)-(spacer)-(ligand moiety) structure as depicted in FIG. 2.

Figure 3:
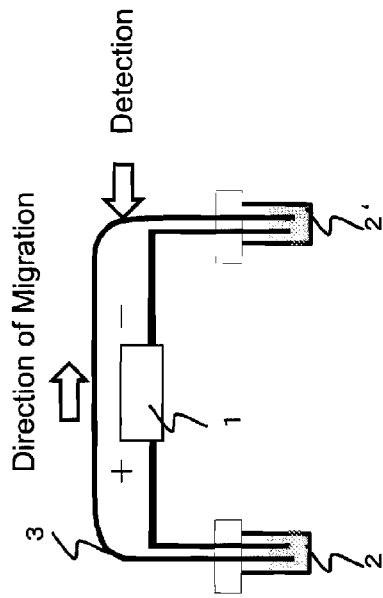
FIG. 3 illustrates a capillary electrophoresis apparatus for use in a method for qualitatively and quantitatively analyzing uranium according to the present invention.

FIG. 3 is a diagram illustrating a capillary electrophoresis apparatus used in the method for qualitatively and quantitatively analyzing uranium according to the present invention. First, capillary 3 is flushed and then filled with a migration solution. Next, the anode-side vial containing the migration solution is replaced by a vial containing a sample solution containing a fluorescent uranium complex formed of FTC-PDA and $UO_2^{2+}$ ion in order to allow the sample solution to be injected into the capillary 3 by a pressure difference (by applying pressure or siphoning action). After injection of the sample solution, the vial containing the migration solution is quickly returned to its original position. As an electric field is applied by a power supply 1, the complex migrates in the migration solution within capillary 3 toward the cathode-side migration solution 2'. At the position of detection, laser light is irradiated onto the migrating complex to cause the complex to emit fluorescence. The intensity of the fluorescence is then measured to enable qualitative and quantitative analysis of uranium.

EXAMPLES

The present invention will now be described with reference to Examples, which are not intended to limit the present invention.

Synthesis of FTC-PDA

An acid mixture composed of 5 mL nitric acid (GR (Guaranteed Reagent) grade undiluted solution from Wako Pure Chemical Industries Ltd.) and 10 mL sulfuric acid (GR grade undiluted solution from Wako Pure Chemical Industries Ltd.) was added to 0.5 g of 2,9-dimethyl-1,10-phenanthroline (Wako Pure Chemical Industries Ltd.) and the mixture was heated to 115° C. for 1 hour. To the resulting solution, 100 g of ice was added and the pH of the chilled solution was adjusted to 8.0 by the addition of sodium hydroxide. The resulting precipitate was separated by filtration and dried at 110° C. to give 5-nitro-2,9-dimethyl-1,10-phenanthroline as shown by the formula (B) in FIG. 1.

Subsequently, 1 g of 5-nitro-2,9-dimethyl-1,10-phenanthroline was mixed with 1 g of selenium dioxide and the mixture was dissolved in 5 mL of a 96% aqueous dioxane solution. The resulting solution was refluxed for 3 hours and was then filtered through Celite® pad (Celite Corporation) to obtain the dialdehyde compound shown by the formula (C) in FIG. 1 as a yellow-red precipitate. The dialdehyde compound was refluxed for 3 hours with 10 mL of nitric acid (GR grade undiluted solution from Wako Pure Chemical Industries Ltd.) and the resulting solution was chilled in an ice bath to form a precipitate. The precipitate was recrystallized from an aqueous tetrahydrofuran solution to obtain the compound of the formula (1).

110 mg of the compound of the formula (1) were dissolved in 5 mL of ethanol. To this solution, 15 mg of palladium catalyst (palladium on carbon purchased from Sigma-Aldrich, 10% loading of palladium) were further added and hydrogenation/reduction was carried out under a hydrogen gas pressure of 60 psi to form a solution containing the compound of the formula (2). Upon exposure to air, the solution has changed from yellow to bright red in color. To the discolored solution, 10 mL of 3M hydrochloric acid were added and the palladium catalyst was removed by filtration. Ethanol was then evaporated at 0° C. under reduced pressure. While the solution was stirred, 0.42 mL of a chloroacetyl chloride solution diluted with 20 mL dichloromethane were added and the solution was kept stirred at room temperature overnight. The resulting two-phase mixture was distilled under reduced pressure to form a solid product. This solid product was washed with 10 mL cold water and then dried under reduced pressure to obtain the compound of the formula (3).

100 mg of the compound of the formula (3) were reacted with 20 mL of aqueous ammonia at 25° C. for 16 hours in a sealed system in a sealed tube to obtain the compound of the formula (4).

60 mg of the compound of the formula (4) were suspended in 2 mL of a $10^{-2}$ M aqueous maleic acid buffer and 2 mL of tetrahydrofuran were added to this suspension and dissolved. 68 mg of fluorescein-4-isocyanate of the formula (5) (Sigma-Aldrich) were further added and the mixture was placed in a dark place and heated at 40° C. for 12 hours. Subsequently, FTC-PDA, the compound of the present invention, was separated from the reaction product using a high-performance liquid chromatography (HPLC) apparatus (HPLC-2000 from JASCO) and column chromatography (Hypersil BDS C18 from Thermo Scientific Japan). Acetonitrile (solution A) and a 0.1% aqueous trifluoroacetic acid solution (solution B) were used as the mobile phase in a gradient system, in which the volume ratio of A to B (A/B) was 5/95 at the beginning of the elution and kept at 5/95 for the first 6 min, and then at 40/60 from after 6 min until after 15 min, and then at 90/10 from after 15 min until after 20 min. The flow rate of the mobile phase was kept at 1.20 mL/min and the column temperature at 30° C. The peak appeared 18.4 min after the elution was started and the eluate collected at this point was stripped of the solvent under reduced pressure to obtain 52 mg of the purified compound of the present invention (FTC-PDA).

Preparation of Solutions (1) Preparation of Aqueous Solution of Uranium Detection Fluorescent Probe Purified FTC-PDA was weighed and dissolved in ultrapure water to prepare a $10^{-3}$M aqueous solution. In cases where FTC-PDA does not dissolved in ultrapure water, a sodium hydroxide solution (Ultrapur grade from Kanto Chemical) is added.

(2) Preparation of Uranium Solution

A uranium standard solution determined by ICP-MS (Inductively Coupled Plasma Mass Spectrometer) was diluted to prepare a 0.1M nitric acid solution containing $2.0 \times 10^{-5}$ uranium.

(3) Preparation of Aqueous Boric Acid Solution

Boric acid (99.9999% purity from Merck) was dissolved in ultrapure water to prepare a 0.1 M aqueous boric acid solution and the pH of the aqueous solution was adjusted to 10.0 by the addition of a sodium hydroxide solution (Ultrapur grade from Kanto Chemical Co., Inc.).

(4) Preparation of an aqueous solution of trans-1,2-diaminocyclohexane-N,N,N',N'-tetraacetic acid (CyDTA)

CyDTA (99.0% purity from Dojindo Molecular Technologies) was dissolved in ultrapure water to prepare a $10^{-3}$M aqueous CyDTA solution. In cases where CyDTA does not dissolved in ultrapure water, a sodium hydroxide solution (Ultrapur grade from Kanto Chemical Co., Inc.) is added.

Preparation of Sample Solutions

The above-described uranium detection aqueous fluorescent probe solution, the uranium solution and the aqueous boric acid solution were mixed together. To the mixture, a 3 M aqueous sodium hydroxide solution (Ultrapur grade from Kanto Chemical Co., Inc.) was added to prepare a sample solution containing $5.0 \times 10^{-7}$ M uranium detection fluorescent probe, $5.0 \times 10^{-8}$ M uranium and $2.0 \times 10^{-2}$M boric acid and having a pH in the range of 9.6 to 10.0.

Preparation of Migration Solution

The above-described aqueous boric acid solution and the aqueous CyDTA solution were mixed together and the above-described 3 M aqueous sodium hydroxide solution was added to prepare a migration solution containing $2.0 \times 10^{-2}$M boric acid and $2.5 \times 10^{-5}$M CyDTA and having a pH 10.0.

Capillary Electrophoresis

The electrophoresis apparatus used was G 7100 available from Agilent Technologies. A laser-induced fluorescence detector (ZATALIF Discovery from Picometrics) was used as the detector along with Blue Solid-State Laser System 85-Z48804 available from Melles Griot with the excitation wavelength of 488 nm as the laser source. The capillary used was a fused silica capillary equipped with a collecting lens (available from Picometrics; inner diameter=50 μm, outer diameter=375 μm, entire length=69 cm, effective length=50 cm).

Figure 4:
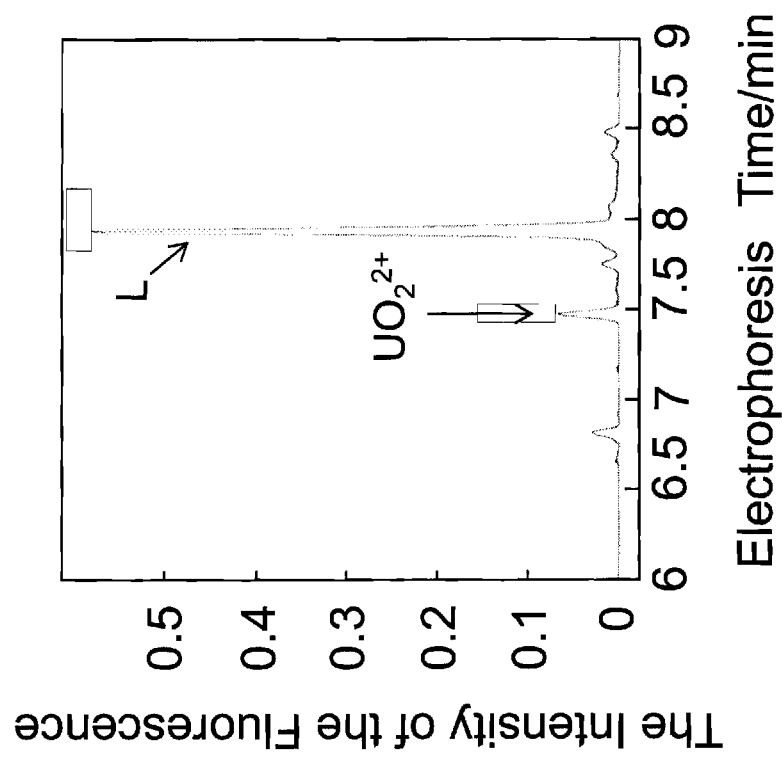
FIG. 4 illustrates the results of the capillary electrophoresis.

The capillary was sequentially washed with a 1 M aqueous sodium hydroxide solution for 20 min, with ultrapure water for 20 min, and then with the above-described migration solution for 10 min. The capillary was then filled with the migration solution. 5 nL of the sample solution was introduced into the capillary from the anode side by applying a pressure of 50 mbar for 5 seconds. A voltage of 20 kV was then applied and the temperature of the electrophoresis apparatus was kept at 25° C. during electrophoresis. The laser power of the laser-induced fluorescence detector was 8 mA and the voltage of the photomultiplier was 570 V. FIG. 4 shows the results of the electrophoresis. As shown, a peak representing the fluorescent uranium complex formed of FTC-PDA and $UO_2^{2+}$ ion (indicated by $UO_2^{2+}$ in FIG. 4) and a peak representing FTC-PDA (indicated by L in FIG. 4) were detected. This demonstrates that qualitative analysis of uranium can be achieved by capillary electrophoresis using FTC-PDA as a fluorescent probe for the detection of uranium.

Furthermore, it is also demonstrated that quantitative analysis can be achieved by the calibration curve method. The detection limit of uranium was in the order of $3.5 \times 10^{-10}$ M. It should be noted that capillary was washed with the migration solution for 5 min between each analysis.

As described above, the compound of the present invention is capable of forming a stable fluorescent uranium complex with $UO_2^{2+}$ ion. The complex can migrate in a capillary during capillary electrophoresis and the intensity of the fluorescence emitted by the complex can be measured. Thus, the compound of the present invention can be used as a fluorescent probe in the qualitative and quantitative analysis of uranium using less expensive electrophoresis apparatuses.

REFERENCE NUMERALS

1 Power supply
2, 2' Migration solution
3 Capillary

We claim:
1. A compound of the formula:

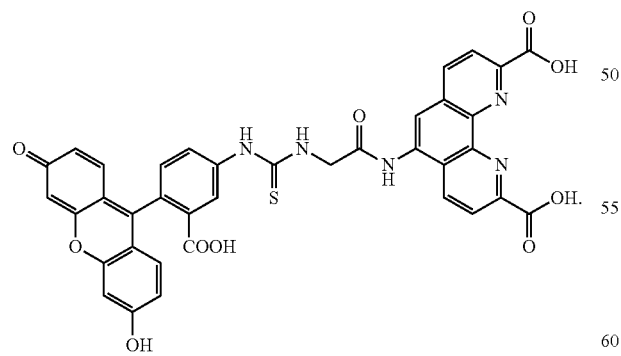

2. A method for synthesizing the compound according to claim 1, the method comprising steps of:
reacting a compound of the following formula (1) with hydrogen to obtain a compound of the following formula (2) (Step (a));

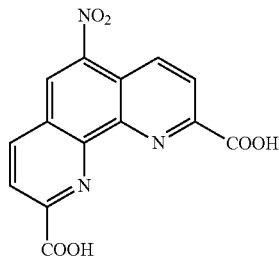

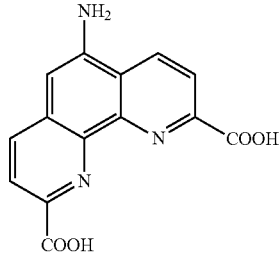

reacting the compound of the formula (2) with chloroacetyl chloride to obtain a compound of the following formula (3) (Step (b));

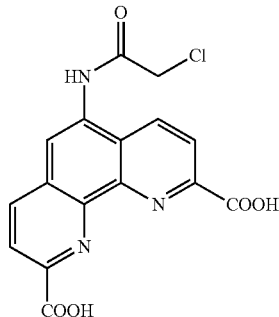

reacting the compound of the formula (3) with an aqueous ammonia to obtain a compound of the following formula (4) (Step (c)); and

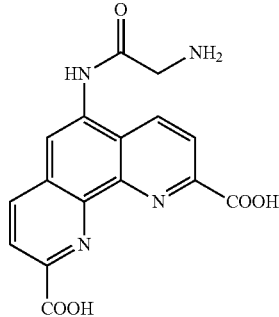

reacting the compound of the formula (4) with fluorescein-4-isocyanate of the following formula (5) (Step (d)).

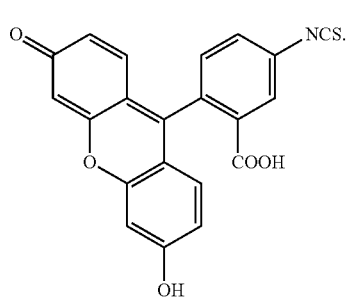

(5)

3. A fluorescent probe for detecting uranium, the probe comprising the compound according to claim 1.

4. A method for qualitatively and quantitatively analyzing uranium, the method comprising steps of:
   mixing a sample containing uranium with the fluorescent probe for detecting uranium according to claim 3 to form a fluorescent uranium complex in the resulting mixture (Step (A));
   subjecting the mixture containing the fluorescent uranium complex to capillary electrophoresis (Step (B)); and
   measuring the intensity of fluorescence (Step (C)).

\* \* \* \* \*